United States Patent [19]
Gadberry

[11] Patent Number: 5,476,475
[45] Date of Patent: Dec. 19, 1995

[54] TROCAR WITH UNIVERSAL SEAL PROTECTOR

[75] Inventor: Donald L. Gadberry, San Clemente, Calif.

[73] Assignee: Applied Medical Resources, Laguna Hills, Calif.

[21] Appl. No.: 267,845

[22] Filed: Jun. 29, 1994

Related U.S. Application Data

[63] Continuation of Ser. No. 979,835, Nov. 23, 1992, abandoned.

[51] Int. Cl.[6] .............................. A61B 17/00; A61M 5/00; F16K 51/00
[52] U.S. Cl. ........................ 606/185; 604/167; 604/264; 251/149.1
[58] Field of Search ................... 604/247, 264, 604/167; 251/149.1, 149.2, 149.7; 606/185, 191, 184, 1

[56] References Cited

U.S. PATENT DOCUMENTS 1,800,045  4/1931  Bates ................................ 251/149.2
3,620,500  11/1971 Santomieri ........................ 251/149.1
4,387,879  6/1983  Tauschinski ..................... 251/149.1
5,176,652  1/1993  Littrell ............................... 251/149.1
5,180,373  1/1993  Green et al. .

*Primary Examiner*—Tamara L. Graysay
*Attorney, Agent, or Firm*—Richard L. Myers

[57] ABSTRACT

A trocar is adapted to provide a working channel across a body wall to accommodate a surgical instrument having a sharp or puncture prone configuration. The trocar includes a cannula and a housing which encloses at least one septum seal. A valve adjuster is movable by the instrument from a first position and a relaxed state, to a second position and an expanded state wherein the valve protector is disposed at least partially between the instrument and the valve. In this second position axial friction is reduced and the valve is protected from the sharp or puncture prone configuration of the instrument. A method includes the steps of engaging the valve adjuster with the instrument and moving the adjuster from the first position to the second position.

20 Claims, 2 Drawing Sheets

TROCAR WITH UNIVERSAL SEAL PROTECTOR

This application is a continuation of application Ser. No. 07/979,835, filed Nov. 23, 1992, now abandoned.

BACKGROUND OF THE INVENTION

1. Field of the Invention

This invention relates generally to trocars having valves which seal against instruments operable through a working channel in the trocar.

2. Discussion of the Prior Art

Mechanical trocars typically included a cannula defining a working channel, and a housing which encloses valves that function to inhibit the escape of insufflation gasses. The cannula of the trocar is adapted to be positioned across the abdominal wall of a patient using an obturator which is initially inserted into the working channel and then removed once the cannula is in place. Various elongate instruments can be inserted through the working channel of the trocar to reach, and perform operative functions, at a site within the abdomen. It is the function of the valves to engage the outer surface of such an instrument and form seals around the instrument to prevent the escape of insufflation gasses.

Trocar valves are commonly formed from elastomeric materials which are highly susceptible to puncture and tearing by sharp instrument configurations. Since many instruments, and of course the obturator, typically have sharp distal tips, it has become particularly desirable to protect the valves from these objects.

In some cases the valves have been operable by lever arms which have provided the valves with variable diameters. In such a configuration, protective shields have been provided for attachment to the obturators. These shields have functioned with the lever arms to expand the valve. Shields have also been designed to extend between the seal and the sharp distal tip of the obturator as disclosed and claimed in applicant's copending application Ser. No. 07/909,075, filed Jul. 2, 1992 and entitled Seal Protection Mechanisms, now abandoned, which is incorporated herein by reference. Such shields have been adapted solely for use with obturators and are not necessarily applicable to other types of instruments.

Other valve protectors have functioned relative to the lever arms in response to insertion of any instrument into the working channel. Such a mechanism is disclosed and claimed in applicant's copending application Ser. No. 07/952,300 filed on Sep. 28, 1992 and entitled Seal Protection Mechanism, which is incorporated herein by reference.

In spite of these advances in the art, it has remained desirable to provide a mechanism which can protect an ordinary septum valve devoid of any lever mechanism and also to limit friction on the instrument during axial passage through the valve. In the absence of a protection mechanism for the ordinary septum seal, instruments having sharp tips have been free to engage the valve often resulting in damage to the valve which renders the entire trocar inoperable. Even in those instances where the valve is not cut or otherwise damaged, large instruments which are required to move through a small orifice in a septum valve have experienced significant friction forces making axial movement of the instrument difficult.

SUMMARY OF THE INVENTION

In accordance with the present invention, a trocar is provided with a valve expander which is movable from a first position spaced from the valve to a second position in proximity to the valve. The valve expander has a first configuration in a relaxed state and a second configuration in an expanded state. When an instrument is inserted into the trocar, it engages the valve expander at the first position and moves it axially into proximity with the valve. When the expander initially contacts the valve, it is generally in its relaxed state. Further axial movement of the instrument causes the expander to move the remainder of its stroke to the second position while at the same time moving the valve radially outwardly enlarging the orifice of the valve. In this second position, the valve expander is disposed between the instrument and at least a portion of the valve.

Once the instrument is operatively disposed it is necessary to move the valve adjuster in order to permit the valve to form a seal with the instrument. This can be accomplished by withdrawing the instrument slightly to move the adjuster from the second position back to the first position. This movement may be assisted by a spring which biases the adjuster to the first position.

In a first aspect of the invention, a trocar is adapted to provide a working channel across a body wall to accommodate a surgical instrument. The trocar includes a cannula which defines the working channel along an axis extending between a distal end and a proximal end of the cannula. A housing attached to the cannula at the proximal end encloses at least one valve which is configured to form a seal around the instrument and across the working channel. Valve protection means protects the valve from the instrument and is movable from a first position spaced from the valve to a second position wherein the protection means extends at least partially between the instrument and the valve. The valve protection means is responsive to insertion of the instrument to move from the first position to the second position.

A second aspect of the invention involves a method for protecting a valve disposed in a trocar having a working channel extending through an orifice in the valve. The method comprises the steps of providing the trocar with a valve adaptor movable from the first position spaced from the valve to a second position in proximity to the valve, the valve protector in the second position being disposed to enlarge the orifice of the valve. The method also includes the steps of inserting an instrument into the working channel and during the inserting step engaging the valve protector at the first position. Moving the valve protector with the instrument from the first position to the second position enlarges the orifice of the valve to protect the valve and reduce friction on the instrument. This movement may be assisted by a spring which biases the expander to the first position.

These and other features and aspects of the present invention will be more apparent with a detailed description of the preferred embodiments and reference to the associated drawings.

DESCRIPTION OF PREFERRED EMBODIMENTS

Figure 1:
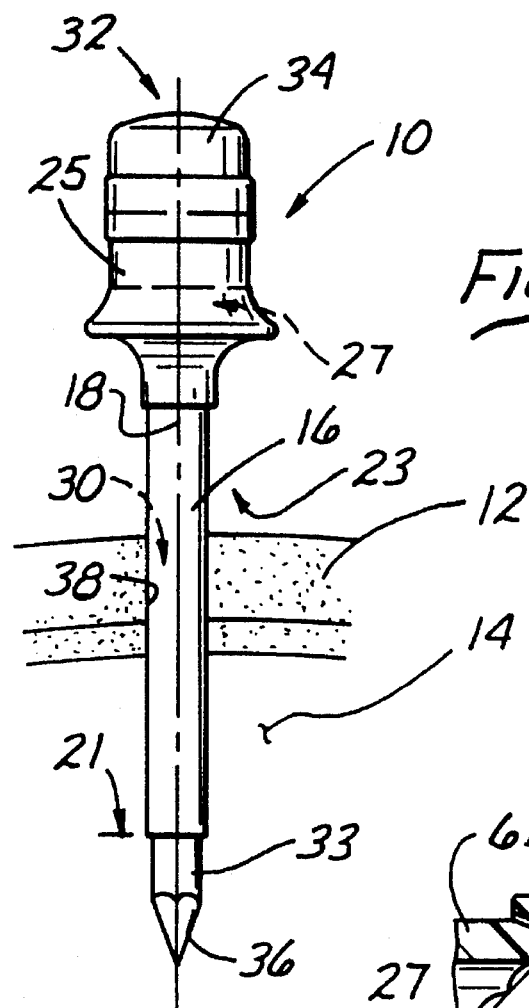
FIG. 1 is an side elevation view of a trocar with its cannula disposed in an operative position across a body wall.

A trocar is illustrated in FIG. 1 and designated generally by the reference numeral 10. The purpose of the trocar 10 is to establish a working channel across a body wall, such as the abdominal wall 12. The trocar 10 extends from regions exterior of the body to regions interior of the body, such as the abdominal cavity 14. The trocar 10 is commonly used in laparoscopic surgery wherein the abdominal cavity 14 is pressurized with an insufflation gas in order to provide for organ separation and otherwise increase the size of the operative environment.

The trocar 10 includes a cannula 16 which extends along an axis 18 between a distal end 21 and a proximal end 23. At the proximal end 23, a housing 25 is attached to the cannula 16 and provides an enclosure for a valve seal mechanism 27 which is described in greater detail below. When the trocar 10 is operatively disposed, these elements (the cannula 16, the housing 25, and valve mechanism 27) define a working channel 30 into the cavity 14. Various instruments, such as scopes, clamps and staplers, can be inserted through this channel 30 to perform operative functions in the cavity 14. These instruments, which will typically have elongate shafts and sharp distal tips, are collectively represented by the instrument 41 in FIG. 2.

Placing the cannula 16 in its operative position is accomplished by using an obturator 32 which has an elongate spike or shaft 33 with a cap 34 disposed at its proximal end. Of importance to the present invention is a sharp tip 36 which is disposed at the distal end of the obturator shaft 33. It is the purpose of the obturator 32 to place the cannula 16 in its operative position across the abdominal wall 12. To accomplish this function, the obturator 32 is initially loaded into the working channel 30 by moving the sharp tip 36 through the seal mechanism 27 in the housing 25. With the sharp tip 36 disposed distally of the cannula 16, the obturator 32 and the cannula 16 are forced through the abdominal wall 12 to create a puncture or hole 38. Once the hole 38 has been created and the cannula 16 is in its operative position, as illustrated in FIG. 1, the obturator 32 can be removed from the working channel 30 through the housing 25 and the seal mechanism 27.

Once the trocar 10 is operatively disposed and the obturator 32 has been removed, additional insufflation gasses can be introduced into the cavity 14 to enlarge the surgical environment. The insufflation gas, which commonly includes carbon dioxide, can be introduced through the working channel 30 of the trocar 10. Laparoscopic instruments which include retractors, scalpels, staplers and clamps, for example, are all represented by the instrument 41 illustrated in FIGS. 2 and 3. Such instruments will typically have an elongate cylindrical configuration and may have a sharp distal tip.

It is the purpose of the seal mechanism 27 to block the escape of insufflation gasses from the cavity 14 through the working channel 30 of the trocar 10. This blockage is required not only when the instrument 41 is absent from the working channel 30, but when the instrument 41 is operatively disposed within the trocar 10.

Figure 2:
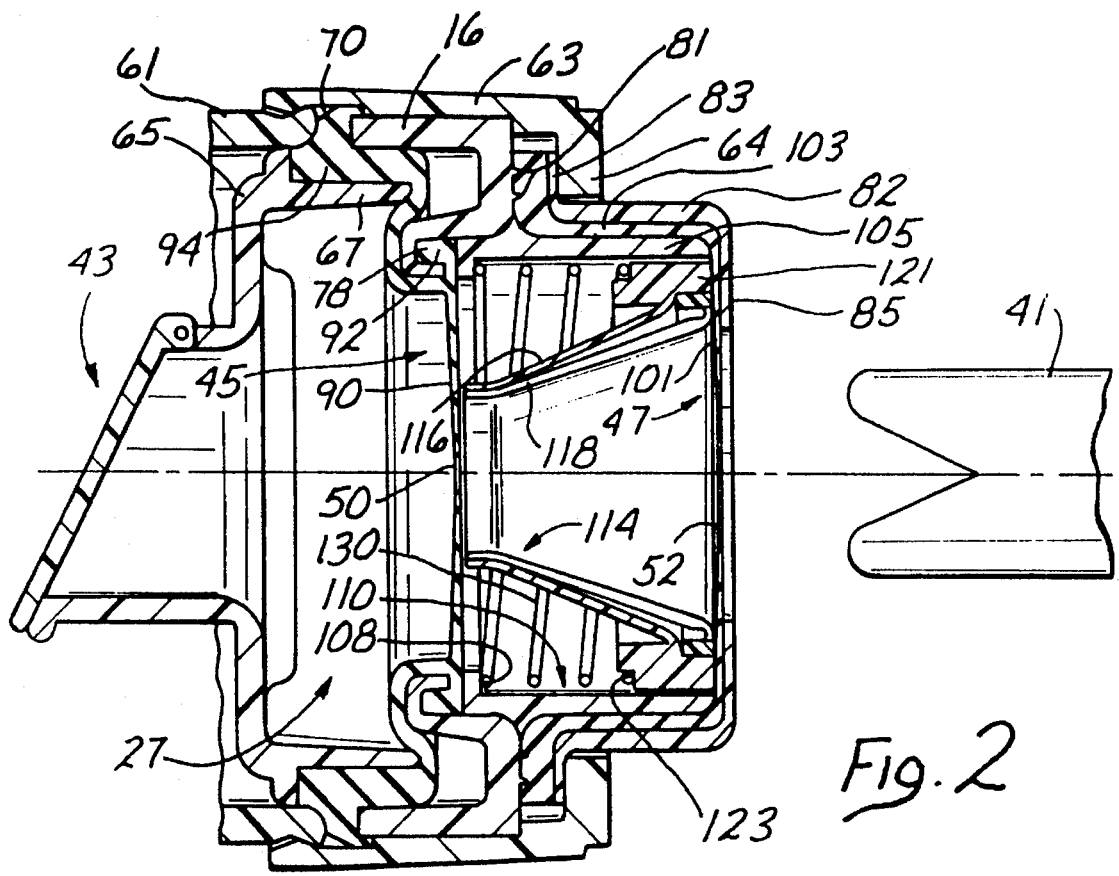
FIG. 2 is an axial cross-section view of a valve housing associated with the trocar of FIG. 1, a valve adjuster in the housing is illustrated in a first position and a relaxed state.

Referring now to FIG. 2, the seal mechanism 27 can take many different forms, but in the illustrated embodiment, a flapper valve 43 is provided along with a pair of septum valves 45 and 47. Each of the septum valves 45 and 47 extends generally radially of the axis 18 and defines a hole or orifice 50 and 52 respectively, along the working channel 30. It is these valves 45, 47 which are intended to engage the outer surface of the obturator 32 or instrument 41, in order to form a seal across the working channel. Since these instruments have various diameters, it is important that the valves 45, 47 be formed of elastomeric materials so that the respective orifices 50, 52 can vary in size.

The greater the range of instrument diameters to be accommodated, the greater the need for compliance in the valves 45, 47. This compliance generally results from the elastomeric characteristics of the valves 45, 47. Where a particularly large range of instrument diameters is to be accommodated, it is customary to provide multiple valves each having a different orifice size. Such is the case with the embodiment of FIG. 2 where the orifice 52 of the valve 47 is about 6 mm in diameter and the orifice 50 of the valve 45 is about 3 mm in diameter.

The greater the requirement for diameter accommodation or compliance, the greater the need for elasticity in the material forming the valves 45, 47. But this elasticity also makes the valves 45, 47 particularly susceptible to sharp edges and points which are typically associated with the obturator 32 and other instruments, such as the instrument 41.

Figure 3:
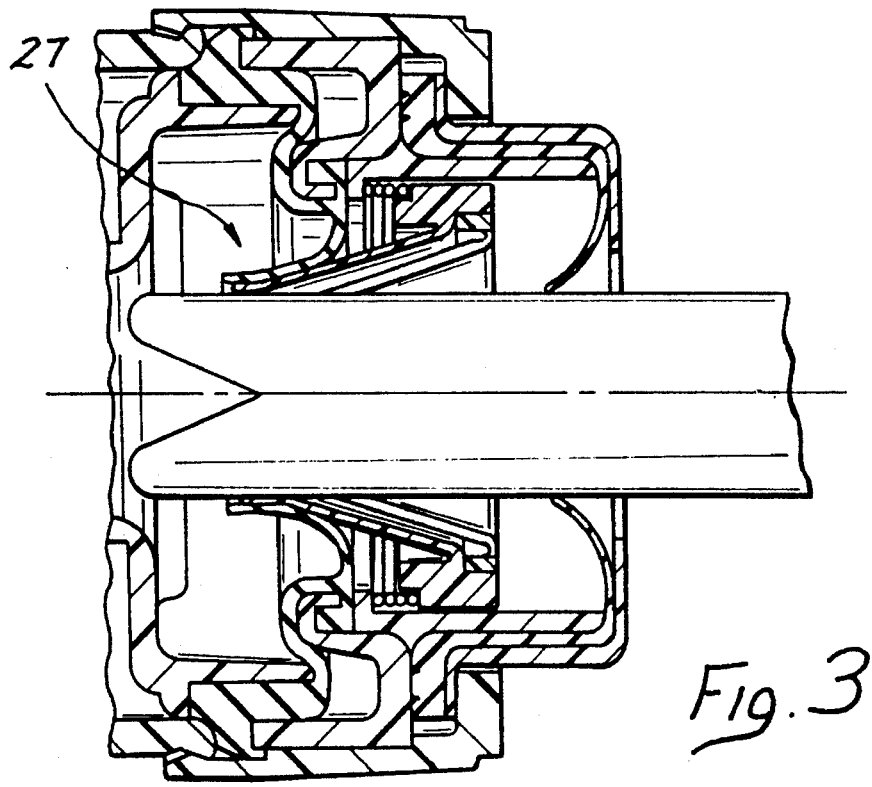
FIG. 3 is an axial cross-section view similar to FIG. 2 wherein the valve adjuster is illustrated in a second position and an expanded state.

In a preferred embodiment, the septum valves 45, 47 are mounted within the housing 25 by several elements each of which has an annular configuration and a cross-sectional shape as illustrated in FIGS. 2 and 3. For example, the housing 25 may include a body member 61, and a cap 63 which is fixed (for example with a snap fit) to the body member 61. In the illustrated embodiment, the cap 63 has a radial flange 64. Generally interiorly of the member 61 and the cap 63 are several elements which function to mount the flapper valve 43 and the septum valves 45, 47 to perform their respective functions. In the illustrated embodiment, the flapper valve 43 is mounted on a flapper valve support 65 which includes an annular flange 67. This flange 67 defines a cavity 70 with the body member 61 and cap 63.

A septum valve support 76 is disposed proximally of the valve support 65 and includes portions defining an axial groove 78. The septum valve support 76 also includes a pair of annular projections 81 which extend axially proximally within the housing 25. Seated within the flange 64 of the cap 63 is a cover 82 having an outwardly extending flange 83 and an inwardly extending flange 85.

The body member 61 and cap 63 together with the supports 65, 76 and the cover 61 are all formed from a rigid material such as an injection molded plastic. It is the purpose of these elements to house the valves 43, 45 and 47 and to support these valves in their function to maintain insufflation pressures. This function includes not only the capability of forming a seal with the obturator 32 or instrument 41, but also to form a seal with the housing 25.

A configuration of particular interest for the valve 45 is illustrated in FIG. 2. This embodiment of the valve 45 includes not only a septum 90, but also an annular flange 92 which is seated within the axial groove 78 of the seal support 76. Integral with the septum 90 is an extension 94 of the valve 45 which extends radially outwardly and terminates in the annular cavity 70. When the cap 63 is forced onto the body member 61, this extension 94 is compressed between the member 61, the cap 63 and the valve support 65. In this manner, the valve 45 forms a seal with the housing 25 of the trocar 10.

The valve 47 also includes a septum 101 and an integral extension 103 which is disposed inwardly of the cover 82 and is sandwiched between the cover 82 and the valve support 76 when the cap 63 is snap fit to the body member 61. In this location, the extension 103 is forced against the annular projections 81 thereby forming a seal between the housing 25 and the valve 47.

Of particular interest to the present invention is a separator 105 which is disposed between the septums 90 and 101 of the respective valves 45 and 47. The separator 105 has a generally cylindrical configuration, one end of which abuts the septum 90 maintaining the flange 92 within the axial groove 78. The other end of the separator 105 abuts the septum 101 maintaining the valve 47 against the inner surface of the cover 82. This separator 105 includes a proximally facing shoulder 108 which defines in part a guideway 110 that extends axially of the trocar 10 and has an annular configuration in the illustrated embodiment.

As previously noted, the orifice 50 associated with the valve 45 is smaller than the orifice 52 associated with the valve 47. Thus the septum 90 of the valve 45 extends inwardly further than the septum 101 of the valve 47. As a consequence, an instrument having a relatively small diameter may pass through the orifice 52 without touching the septum 101. However, it is intended that such an instrument with a smaller diameter would not pass through the orifice 50 and would therefore form a seal with the septum 90. In this instance, the valve mechanism 27 relies upon the valve 45 to form a seal with the instrument 41.

A problem addressed by the present invention occurs when an instrument, such as the instrument 41, with the diameter larger than the orifice 52 is inserted into the trocar 10. In this instance, the instrument 41 would contact the valve 47 and form the desired seal with the septum 101. As the instrument 41 is inserted further into the trocar 10, it might also contact the septum 90 due to the smaller orifice 50. Under these circumstances, a significant portion of the septum 90 would engage the outer surface of the instrument 41 creating undesirable friction or drag which would hinder the axial movement of the instrument 41. In such a case where the seal is formed primarily by the valve 47, it is desirable to reduce the friction between the valve 45 and the instrument 41. Of equal importance is the desirability to protect the valve 45 from any sharp configuration which may be associated with the obturator 32 or instrument 41. These functions are accomplished in a preferred embodiment by enlarging the orifice 50 formed by the septum 90 of the valve 45.

In a preferred embodiment a valve adjuster 114 is provided with an interleaved configuration such as that disclosed in applicant's copending application Ser. No. 07/952,300 filed on Sep. 28, 1992 and entitled Seal Protection Mechanism. This application is incorporated herein by reference and discloses a structure including a pair of outer leaves 116 which alternate with a pair of inner leaves 118 to form an expandable funnel. The outer leaves 116 are mounted on an annular support 121 which includes a distally facing shoulder 123. This support 121 is slidable within the guideway 110 between a first position in proximity to the valve 47, as illustrated in FIG. 2, and a second position in proximity to the valve 45 as illustrated in FIG. 3.

In the first position, the valve adjuster 114 will be in a relaxed state with the leaves 116 and 118 extending inwardly from the valve 47 toward the valve 45, to a radius typically not less than the radius of the orifice 52. With this configuration, an instrument smaller than the orifice 52, such as a 5 mm instrument, would contact neither the septum 101 nor the leaves 116, 118, but would contact the septum 90 and form a seal with the valve 45.

When an instrument having a diameter larger than the orifice 52 is inserted into the working channel 30, it initially contacts the septum 101 to form a seal with the valve 47. Further axial movement of the instrument 41 engages the leaves 116, 118 in the relaxed state and begins to move the valve adjuster 114 axially distally along the guideway 110. With further axial movement of the instrument 41, the leaves 116, 118 are brought into engagement with the septum 90 of the valve 45. In this position, the septum 90 retards axial movement of the adjuster 114 so that further insertion of the instrument 41 tends to cause the leaves 116, 118 to expand outwardly. With the adjuster 114 in contact with the septum 90, its outward expansion together with further axial movement causes the septum 90 to stretch outwardly thereby enlarging the orifice 50. This of course reduces frictional drag on the instrument 41.

In this second position, the adjuster 114 is disposed between the instrument 41 and at least a portion of the septum 90. In a particular embodiment, it may be desirable that the adjuster 114 extend entirely between the instrument 41 and the septum 90 so that the valve 45 is completely removed from contact with the instrument 41. Such an embodiment is illustrated in FIG. 3 where contact between the valve 45 and the instrument 41 is inhibited by providing the leaves 116, 118 with an axial extension in the second position which is equal to about the length of the septum 90.

In this particular aspect of the invention, which involves the insertion of an instrument having a diameter greater than that of the orifice 52, the insufflation seal is formed by the valve 47 while the valve 45 is at least partially displaced from contact with the instrument 41.

Once the instrument 41 is operatively disposed, it may be desirable to release the septum 90 so that it can form a second seal with the instrument 41. This can be accomplished by moving the valve adjuster 114 from the second position back to the first position thereby permitting the septum 90 to contact the instrument 41. This movement can be facilitated by withdrawing the instrument 41 slightly thereby applying a proximal force to the adjuster 114. This movement from the second position to the first position may also be facilitated by placing a compression spring 130 in the guideway 110 to seat against the shoulder 108 of the separator 105 and the opposing shoulder 123 of the support 121.

A preferred method associated with the invention involves a trocar having at least one valve such as the valve 45 disposed in the housing 25. Such a method might include the step of providing a valve adjuster 114 movable from the first position spaced from the seal 45 to a second position in proximity to the seal 45. In this second position, the valve adjuster 114 would be disposed to at least enlarge the orifice 50 of the valve 45 and perhaps entirely remove the septum 90 from the working channel 30. Then by inserting an instrument 41 into the working channel, it would initially engage the valve adjuster 114 at the first position and then move the adjuster axially from the first position to the second position.

During movement along this path, the method may include the steps of initially contacting the valve adjuster 114 in a relaxed state and then sliding the adjuster from the first position into contact with the septum of the valve 45. After engaging the septum 90, with the adjuster 114 typically in the relaxed state, further axial movement of the instrument 41 would result in expanding the adjuster 114 and the septum 90 radially outwardly to enlarge the orifice 50.

In an embodiment wherein the valve 45 is totally isolated from the instrument 41, the method may include the step of withdrawing the instrument to displace the adjuster 114 from the second position. This step of withdrawing could be facilitated by biasing the adjuster 114, for example with the spring 130, to move the adjuster 114 from the second position back to the first position.

Figure 4:
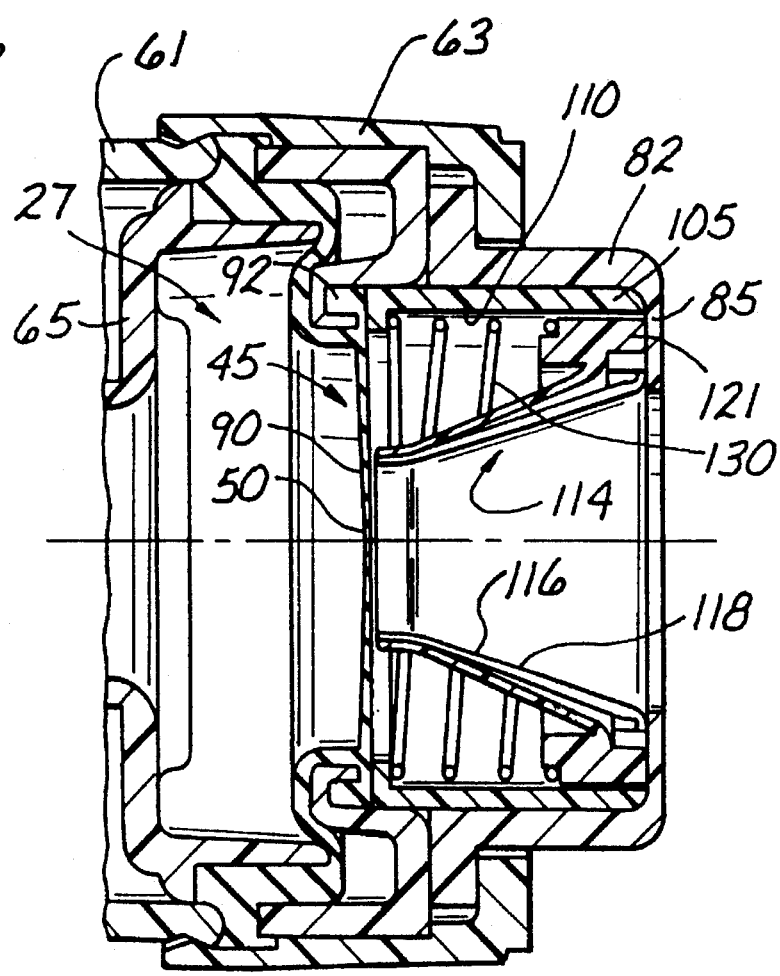
FIG. 4 is an axial cross-section view of a further embodiment of the invention including a single valve and an associated valve adjuster.

In a further embodiment of the invention illustrated in FIG. 4, the trocar 10 includes but a single valve 45. Even in this embodiment, the advantages associated with the valve adjuster 114 are apparent. As previously discussed, an instrument, such as the instrument 41, can be inserted into the trocar 10 to engage the valve adjuster 114. Further movement of the instrument can move the septum 90 associated with the valve 45, enlarging the orifice 50 and inhibiting the frictional engagement of the instrument 41 by the seal 45. In this manner, the valve 45 is protected from any sharp configuration of the instrument 41 until the instrument has been fully inserted. Then the adjustor 114 can be moved back to the first position to create the desired seal between the valve 45 and the instrument 41. In this embodiment, the separator 105 abuts the flange 85 of the cover 82. In addition, the annular support 121 is positioned against the flange 85 when the valve adjuster 114 is in the first position.

The valve adjuster 114 could also be provided with many different configurations, as long as it performs the function of displacing the septum 90 during insertion of the instrument 41 to limit friction or otherwise protect the valve 45.

Given the wide variations within this concept, one is cautioned not to restrict the invention to the embodiments which have been specifically disclosed and illustrated, but rather encouraged to determine the scope of the invention only with reference to the following claims.

I claim:

1. A trocar adapted to provide a working channel across a body wall to accommodate a surgical instrument having an outer surface and a distal tip, the trocar comprising:
   a cannula having an axis extending between a distal end and a proximal end of the cannula;
   a housing attached to the cannula at the proximal end of the cannula and forming with the cannula the working channel;
   valve means disposed in the working channel for forming a seal with an outer surface of the instrument and across the working channel;
   a valve adjustment apparatus, at least a portion of which is disposed in the working channel proximally of the valve means, the valve adjustment apparatus being adapted to move axially within said working channel between a first position spaced from the valve means and a second position wherein at least a portion of the valve adjustment apparatus is interposed between the valve means and a portion of the working channel which extends through the valve means, such that the valve means is protected from the instrument when the distal tip of the instrument is inserted therethrough; and
   the valve adjustment apparatus being adapted to be responsive to insertion of the instrument into the working channel to move from the first position to the second position.

2. The trocar recited in claim 1 further comprising apparatus for biasing the valve adjustment means to the first position.

3. The trocar recited in claim 1 further comprising means defining a guideway for guiding the valve adjustment apparatus during movement of the valve adjustment apparatus between the first position and the second position.

4. The trocar recited in claim 3 wherein the guideway is disposed axially of the trocar so that the first position of the valve adjustment apparatus is spaced axially from the second position of the valve adjustment apparatus.

5. The trocar recited in claim 1 wherein the valve adjustment apparatus has a conical inner surface adapted to be engaged by the instrument when the instrument is inserted into the working channel.

6. The trocar recited in claim 1 wherein the valve adjustment apparatus comprises:
   a wall defining a portion of the working channel which extends through the valve adjustment apparatus;
   a continuous inner surface of the wall having a conical configuration and converging with progressive distal positions along the axis of the cannula; whereby
   the conical inner surface of the wall of the valve adjustment apparatus is adapted to be contacted by the instrument when the instrument is inserted into the working channel.

7. The trocar recited in claim 6 wherein the wall of the valve adjustment apparatus is radially expandable to enlarge the working channel through the valve adjustment apparatus to a diameter sufficient to permit passage of the instrument through the valve.

8. The trocar recited in claim 7 wherein axial movement of the instrument through the valve adjustment apparatus produces on the valve adjustment apparatus an axial force component tending to move the valve adjustment apparatus axially between the first position and the second position, and a radial force component tending to radially expand the valve adjustment apparatus between the first position and the second position.

9. A trocar adapted to provide a working channel across a body wall to accommodate a surgical instrument having a particular diameter, the trocar comprising:
   a cannula defining the working channel along an axis between a distal end and a proximal end of the cannula;
   a housing attached to the cannula at the proximal end of the cannula;
   a first septum valve disposed within the housing and having an orifice with a first diameter which is less than the particular diameter of the instrument;
   a second septum valve disposed within the housing and having an orifice with a second diameter which is less than the particular diameter of the instrument and greater than the first diameter of the first valve; and
   valve adjustment means disposed proximally of the first valve for enlarging the first orifice of the first valve, the valve adjustment means being responsive to insertion of the instrument to move from a first position in proximity to the second valve to a second position in proximity to the first valve.

10. The trocar recited in claim 9 wherein the first position is disposed axially of the second position.

11. The trocar recited in claim 9 further comprising means for biasing the valve adjustment means to the first position.

12. The trocar recited in claim 9 wherein the valve adjustment means is dimensioned and arranged to remain in the first position in response to insertion of a second instrument having a diameter less than the second diameter of the second valve.

13. A method for protecting a valve disposed in a trocar having an axis, the trocar having a working channel extending through an orifice in the valve, the method comprising the steps of:

providing in the trocar a valve adjuster movable from a first position spaced from the valve to a second position in contact with the valve, the valve adjuster in the second position being disposed to enlarge the orifice of the valve;

inserting an instrument into the working channel of the trocar, the instrument having an elongate shaft and a sharp or puncture prone configuration;

during the inserting step engaging the valve adjuster at the first position with the instrument;

moving the valve adjuster axially with the instrument from the first position to the second position; and radially expanding the valve adjuster and the valve to enlarge the orifice of the valve.

14. The method recited in claim 13 wherein:

the valve adjuster has a relaxed state and an expanded state;

the contacting step includes the step of contacting the valve with the valve adjuster in the relaxed state; and the expanding step includes the step of moving the valve adjuster to the expanded state with the instrument to enlarge the orifice of the valve.

15. The method recited in claim 13 further comprising the step of biasing the valve adjuster to the first position.

16. A trocar adapted to provide a working channel across a body wall to accommodate a surgical instrument, the trocar comprising:

a cannula defining the working channel along an axis extending between a distal end and a proximal end of the cannula;

a housing attached to the cannula at the proximal end of the cannula;

valve means disposed in the housing for forming a seal around the instrument and across the working channel;

a first septum valve included in the valve means and disposed across the working channel, the first septum valve having an orifice with a first diameter;

a second septum valve included in the valve means and disposed across the working channel, the second septum valve having an orifice with a second diameter greater than the first diameter;

valve adjustment means for protecting the valve means from the instrument, the valve adjustment means disposed between the first septum valve and the second septum valve and being movable in response to insertion of the instrument into the working channel from a first position in proximity to the second septum valve to a second position in proximity to the first septum valve.

17. A trocar adapted to provide a working channel across a body wall to accommodate a surgical instrument having a particular diameter, the trocar comprising:

a cannula defining the working channel along an axis extending between a distal end and a proximal end of the cannula;

a housing attached to the cannula at the proximal end of the cannula;

valve means disposed in the housing for forming a seal around the instrument and across the working channel;

a septum valve included in the valve means and having an orifice with a diameter which is less than the particular diameter of the instrument;

valve adjustment means for protecting the valve means from the instrument, the valve adjustment means being responsive to insertion of the instrument into the working channel to move from the first position spaced from the valve means to a second position wherein the valve adjustment means extends at least partially between the instrument and the valve means when the instrument is operatively disposed in the working channel; and radially expansible means included in the valve means for engaging the orifice of the septum valve to receive the instrument.

18. A method for inserting a surgical instrument through a body wall into a body cavity including the steps of:

providing a trocar having a cannula, a valve housing defining with the cannula a working channel, a valve disposed along the working channel and having elastomeric characteristics for forming a seal around the instrument, and valve adjuster movable from a first position spaced from the valve to a second position wherein the valve adjuster extends at least partially between the instrument and the valve;

providing the valve adjuster with a continuous wall having an inner surface defining the working channel through the valve adjuster;

inserting the instrument into the working channel;

moving the instrument generally axially through the working channel;

during the moving step contacting the continuous inner surface of the wall of the valve adjuster with the instrument to produce on the valve adjuster a radial force and an axial force; and axially advancing the valve adjuster in response to the axial force of the instrument on the valve adjuster to move the valve adjuster from the first position to the second position.

19. The method recited in claim 18 wherein the moving step comprises the step of radially expanding the valve adjuster between the first position and the second position in response to the radial force produced on the valve adjuster by the instrument.

20. The method recited in claim 19 further comprising the step of withdrawing the instrument axially to move the valve adjuster proximally, axially from the second position to a third position wherein the valve adjuster is removed from between at least a portion of the valve and the instrument to facilitate formation of the seal between the instrument and the valve.

* * * * *